United States Patent [19]

Van Dam et al.

[11] Patent Number: 4,664,807

[45] Date of Patent: May 12, 1987

[54] METHOD OF ISOLATING STEROLS IN COMMERCIAL QUANTITIES FROM STEROL-CONTAINING MATERIAL

[75] Inventors: Mathieu J. D. Van Dam; Harrie R. De Lange, both of Veenendaal; Robert Grande, Weesp, all of Netherlands

[73] Assignee: Duphar International Research B.V., Weesp, Netherlands

[21] Appl. No.: 802,622

[22] Filed: Nov. 29, 1985

Related U.S. Application Data

[63] Continuation of Ser. No. 326,032, Nov. 30, 1981, abandoned.

[30] Foreign Application Priority Data

Dec. 2, 1980 [NL] Netherlands ................... 8006548

[51] Int. Cl.$^4$ ............................................. B01D 15/08
[52] U.S. Cl. ..................................... 210/635; 210/656; 260/397.25
[58] Field of Search .................. 210/635, 656, 659; 435/815; 260/397.25

[56] References Cited

U.S. PATENT DOCUMENTS 4,192,811 3/1980 Foster ........................... 260/397.25
4,614,620 9/1986 Konai ............................. 260/397.25

FOREIGN PATENT DOCUMENTS 1180694 1/1985 Canada ......................... 260/397.25

OTHER PUBLICATIONS

Chromatography by Heftmann, Reinhold Pub. Co., N.Y., Ch. 18, pp. 484–497, published 1961.
Introduction of Modern Liquid Chromatography by Snyder et al, second edition, John Wiley & Sons of N.Y., pp. 255–257, 617–626, 634–636, 654–657 and 660 relied on., 1979.
Wycoff, et al, Science 125, pp. 347 and 348, (1957).
Papadopoulos et al., J. Neurochem. 4, pp. 223–228, (1959).
Hirsch et al., J. Biol. Chem., pp. 233 and 311–320, (1958).

Primary Examiner—Ernest G. Therkorn
Attorney, Agent, or Firm—Stevens, Davis, Miller & Mosher

[57] ABSTRACT

The invention relates to a method of isolating sterols in commercial quantities from sterol-containing material by subjecting a solution of this material to a column-chromatographic separation; for isolating cholesterol from cholesterol-containing material, silica gel is preferably used as a column packing and a mixture of, for example, heptane and acetone is preferably used as an eluent.

10 Claims, No Drawings

METHOD OF ISOLATING STEROLS IN COMMERCIAL QUANTITIES FROM STEROL-CONTAINING MATERIAL

This application is a continuation of application Ser. No. 326,032, filed Nov. 30, 1981, now abandoned.

The invention relates to a method of isolating sterols in commercial quantities from sterol-containing material.

Sterols occur in nature in considerable quantities. Of these sterols, cholesterol in particular is of great importance because this compound may be used as a starting-material for the synthesis of various valuable substances such as vitamins and steroid hormones. In order to be able to dispose of sterols in a sufficiently pure form, however, there must be a technically and commercially acceptable method of isolating and, if desired, further purifying the sterol from the sterol-containing material.

In a monography by Robert P. Cook, entitled "Cholesterol" and published in 1958 by Academic Press Inc. in New York, the preparation of cholesterol, i.e. the isolation from natural sources and the purification, on a comparatively large scale, is described on pages 21–24. As isolation methods are to be considered extraction, if desired preceded by saponification, of the cholesterol-containing material, or adduct formation of the alcohol mixture obtained after saponification. This adduct formation, preferably by means of oxalic acid or metal salts, is particularly suitable for the isolation of cholesterol from wool fat, an important source of this sterol. Contaminations related to cholesterol, for example, other wool fat sterols when using wool fat as a source of cholesterol, can be removed by a purification via the dibromide or by means of crystallization from a suitable solvent.

The now most spread method of obtaining sterols, in particular cholesterol, from sterol-containing material is the formation of an adduct with a metal salt, for example, zinc chloride, succeeded by isolation and decomposition of the adduct, after which, if desired, a further purification of the sterol thus obtained may take place by crystallization from a suitable solvent. Such a method is described, for example, in Netherlands Patent Application No. 6706582 and the literature cited therein.

However, this method suffers from the important disadvantage that zinc chloride pollutes the environment and may hence not be drained with the drain water released in the process. However, it is particularly difficult and hence expensive to recover zinc chloride from the drain water. In addition, the adduct precipitation is an equilibrium reaction, as a result of which approximately 10% of the sterol to be obtained remains in solution. It has not proved possible to isolate as yet this sterol present in the filtrate by means of a subsequent addition reaction.

It is the object of the present invention to provide a process of isolating sterols which can be carried out on an industrial scale, and which does not have the above disadvantages. For that purpose, a solution of the sterol-containing material is subjected to a column-chromatographic separation, in which the sterol can be isolated in a high yield from which, if desired by a simple purification, for example a single crystallization from a suitable solvent, the sterol can be obtained in a purity suitable for pharmaceutical application.

It has long been known already to isolate cholesterol by means of adsorption chromatography from wool fat or from alcohols obtained by saponification of wool fat. For example, Lipson in J. Coun. Sci. Ind. Res. Org. 13 (1940), 273–277 described the isolation of cholesterol from wool fat by providing a quantity of wool fat, dissolved in a boiling mixture of 60% petroleum ether (boiling point 50° C.) and 40% benzene, while hot, on a column with alumina, then extracting the suitable zone of the column packing with an acetone-benzene mixture, and working up the extract. The crude cholesterol, obtained in a weight yield of 6% calculated on the wool fat from which was started, could be purified by two recrystallizations from methyl alcohol. Daniel c.s. (D. Daniel, F. Lederer, L. Velluz, Bull. Soc. Chim. Biol. 27 (1945), 218–255) have studied the chromatographic behaviour of a pre-purified fraction of the unsaponifiable part of wool fat. Adsorption of such a mixture, dissolved in petroleum ether, on alumina succeeded by elution with a series of solvents and mixtures of solvents with increasing polarity, yielded 20–30% by weight of a cholesterol fraction from which pure cholesterol could be isolated by recrystallization from methanol. In the laboratory method described by Daniel c.s. there is started from a pre-purified starting material, namely the unsaponifiable part of wool fat from which the aliphatic alcohols have been removed by a treatment with acetone. The pre-purified mixture to be separated is then brought on the column in a concentration of 1 g per 15 ml of solvent. The charge of the column, that is the quantity of mixture to be chromatographed per quantity of adsorbent, is approximately 5% w/w. In the subsequent elution 9 different solvents are used.

Column chromatography as described in the above-mentioned publications has in the course of the years become a conventional laboratory method for isolating and purifying substances. However, when it is tried to perform this method on an industrial scale, a large number of difficulties are encountered which up till now have considerably restricted the technical and commercial applicability of column chromatography on an industrial scale. It is a generally accepted fact that increase in scale of laboratory experiments frequently presents problems; this is the case in particular in chromatography processes, in which it has been found that theoretical models based on laboratory experiments no longer give good satisfaction when the scale is increased. These problems are mainly due to the subtle character of adsorption chromatography in which the interaction of the component or components to be isolated with the adsorbent on the one hand and the eluent on the other hand, differences in adsorption and solubility of the components to be separated, and the individual adsorption of the solvent or the solvents on the adsorbent play a part. In addition there are causes of a more technical and commercial nature which seriously impede the use of column chromatography in the case of isolations on a large scale. If column chromatography on an industrial scale is to result in commercially acceptable results, then the process should be satisfactory as regards charging of the column, retention-time on the column, yield of isolated product and purity hereof. In industrial chromatography it is thus desired to obtain considerable quantities of the isolated component or components in a sufficiently pure condition in a comparatively short period of time. It is just this combination of requirements that is difficult to satisfy in column chromatography. In fact, when sufficient isolated product is to be obtained in a short period of time, a high charge of the column should be associated with a short retention time on the column. Usually, however, this is at the expense of the separation results, as a result of which the eluted product often is insufficiently pure. In the separation method described by Daniel c.s., the charge is approximately 5%. This is surely insufficient for a process on an industrial scale because with such a small charge the dimensions of the column would have to be much too large. In general the charge cannot be increased without objections, because it is generally known in column chromatography that a higher charge always gives a poorer separation.

The retention time on the column may be distinguished in the time of applying and percolating a solution of the material to be separated (in)to the column (application time) and the elution time. A low application—concentration, for example, 1 g per 15 ml of solvent as described by Daniel c.s., causes a long application time and hence makes the process time-consuming and hence less suitable for industrial application. Another disadvantage of a column chromatographic separation, for example, as described by Daniel c.s., is the large quantity of solvent which is necessary to elute the desired product form the column as completely as possible; as a result of this the eluted product is frequently diluted excessively so that distilling-off the solvent from the product required too much time and energy to be able to preform the process in an economically justified manner.

However, in the process according to the present invention it has succeeded to make column chromatography applicable for isolating sterols on an industrial scale, in which the relevant sterol can be isolated from the sterol-containing material in a comparatively short period of time, in a high yield, in an acceptable concentration, and with such a purity that a simple after-treatment is sufficient to achieve a pharmaceutical quality. As will become apparent from the examples, in the conditions indicated and in less than 6 hours kg-quantities of cholesterol can be isolated from approximately 25% cholesterol-containing material, viz. a mixture of wool fat alcohols, in a concentration of 17 g per liter of solvent; yields of cholesterol of more than 90% calculated on the overall quantity of cholesterol present in the wool fat alcohol are easily obtained; the purity of the resulting cholesterol, namely 67%, is sufficient to isolate cholesterol by a single crystallization, for example from a ketone, for example, acetone, from an alcohol or alcohol mixture, for example ethanol or a mixture of isopropanol and methanol, or from acetic acid, in a high crystallization yield with a purity which is acceptable for pharmaceutical application.

The cholesterol not isolated in the main fraction is collected in the side fractions immediately before and after the main fraction. It has been found that these side fractions can easily be chromatographed and yield cholesterol of a sufficient purity. In this manner the cholesterol can be isolated substantially quantitatively from cholesterol-containing material.

It is a surprising aspect of the present invention that the charge of the column can be increased to approximately 40%, which means that up to approximately 40 g of sterol-containing material per 100 g of packing material may be used for the column without noticeably disadvantageously influencing the separation.

An important criterion for the commercial feasibility of a chromatographic process on an industrial scale is the repeated usability of the filler. In suitable reaction conditions the packing of the column may be used many times successively without intermediate purification. Moreover it has proved possible to regenerate the packing material in a very simple manner, for example by washing with a suitable solvent or solvent-mixture in the column, for example with acetone.

As already stated above, the invention relates in particular to isolating cholesterol in commercial quantities from cholesterol-containing material, for example wool fat or conversion products thereof, for example, an alcohol mixture obtained by saponification of wool fat, or an ester mixture obtained by re-esterification of wool fat with a lower aliphatic alcohol. Other sterol-containing materials, if desired after a pre-treatment, are also suitable to isolate sterols in commercial quantities by means of column chromatography, for example, the unsaponifiable part from fish oil and tallow residue of animal and tall oil of vegetable origin. In addition to cholesterol, other sterols, for example isocholesterol, sitosterol, campesterol and stigmasterol, can also be isolated by means of the method in accordance with the invention.

The chromatographic separation process in accordance with the invention is carried out as follows. An adsorption column (if desired, several adsorptions columns) of suitable dimensions, i.e. adapted to the quantity of material to be separated, is packed with a packing material, The ratios between diameter and length of the adsorption column are not of great importance and may vary from 1:2 to 1:40 dependent on the quantity and the nature of the material to be separated. The quantity by weight of packing material is matched to the quantity and the nature of the material to be separated and the compound or compounds to be isolated and is at most ten times the weight of the material to be separated. The great advantage of the comparatively small quantity of packing material which is necessary in the separation process in accordance with the invention is that for industrial application acceptable column dimensions will suffice. In order to enable a good separation in the chromatography column, a homogeneous packing of the column with packing material is a first requirement. For that purpose it is usual to stir the packing material with a liquid, usually the solvent to be used for the material to be separated, and then to pack the column as uniformly as possible, for example while stirring thoroughly, with the resulting slurry; the formation of air bubbles or air ducts in the packing of the column is to be avoided.

A solution of the material to be separated is then brought on the column (columns), it being ensured that the solution is divided over the upper surface of the column packing as uniformly as possible. Separation of the various components of the mixture on the packing material takes place. This process, as well as the subsequent elution, is preferably carried out at room temperature or at a slightly elevated temperature, for example up to approximately 60° C.

The subsequent elution may be carried out under atmospheric pressure or at a slightly higher pressure. The eluent may be introduced on the top side or on the bottom side of the column. The elution is carried out with solvents or mixtures of solvents suitable for the sterol to be eluted. The elution takes place in fractions, that is to say the eluate is collected in fractions. If desired, a fraction collector is used which ensures that the fractions are automatically collected successively. Various methods are available to distinguish between differences in fraction composition, i.e. differences in constituents of the mixture to be isolated, which constituents are dissolved in the eluent.

Variations of, for example, refraction, dielectric constant, UV absorption or IR absorption, or optical rotation may be used separately or in combination with each other so as to be able to determine the transition from one to the other fraction. Thin-layer chromatography or gas-liquid chromatography may also be used to follow the elution process. These measurements may take place batch-wise in the eluate fractions, but they are preferably carried out in the eluate flow itself, for example in a measuring chamber provided in the eluate line. In the chromatographic isolation of sterols in accordance with the invention use is preferably made of the measurement of the rotation by means of a polarimeter, if desired in combination with refraction measurement.

The elution rate mey be represented as a linear rate, i.e. the rate with which the eluate front moves through the column, for example in m/hour, and is then determined by the diameter of the column and the flow of liquid per unit of time.

The optimum elution rate depends on the composition of the mixture to be separated and on the choice of packing material and eluent.

With an inside diameter of the column of 30 cm it has proved possible with a suitable choice of packing material and eluent to isolate more than 4 kg of cholesterol from an approximately 25% cholesterol-containing mixture of wool fat alcohols in less than 6 hours.

During the elution process the elution may be accelerated or retarded as may be desired. For example, the elution rate may be reduced during the critical phases of the elution, that is to say when the composition of the eluate changes, but it may be increased intermediately so when an eluate fraction with constant composition is collected. Of course it should be ensured that the elution is never accelerated to such an extent that this is at the expense of the separation results.

It has proved possible to bring already a following quantity of the mixture to be separated in solution on the column before the elution of the preceding experiment was completed. This method of "overlapping" application may yield a considerable gain in time and hence saving of costs.

After the elution the solvents are recovered by distillation of the eluate fractions. The remaining sterol or sterols may be further purified, if desired, for example by crystallization. As already noted, when using the chromatography process according to the invention, sterols are obtained in such a purity that a simple after-treatment, for example a single crystallization, is sufficient to isolate the sterols in a quantity which is desired for pharmaceutical application.

As a packing material for the column is chosen, for example, alumina, magnesium silicate—for example Florisil, or silica gel.

As eluents are used one or more organic solvents or solvent mixtures.

When during the elution the composition of the solvent is varied, we have gradient elution. These variations may consist in that the composition of the solvent components is varied or that, when the same solvent components are used, their respective concentrations are varied; both variations are often used side by side. Such a gradient elution is often necessary to produce the desired separation in the various constituents of the mixture to be chromatographed. For example, in the chromatographic separation of cholesterol on a laboratory scale in the above-mentioned article by Daniel c.s., the following solvents are successively used for the elution: petroleum ether, petroleum ether and benzene 9:1, petroleum ether and benzene 2:1, petroleum ether and benzene 1:1, benzene and ether 6:1, benzene and ether 1:1, ether, acetone. Such a gradient elution is particularly complicated and very expensive. As a matter of fact, not only must the various solvents and solvent mixtures be stored in separate containers and be dosed on the column from separate storage vessels, the various solvents after the elution must also be recovered each individually and be combined to form the desired solvent mixtures.

Although gradient elution can be used in the isolation process according to the invention, as appears from the examples, it has been found that in the chromatography process according to the invention the use of a single eluent the composition of which is not varied during the whole elution time is very efficacious and gives an excellent separation of the sterol-containing mixture. The liquid for dissolving the mixture to be separated is preferably also chosen to be of the same composition as the eluent. Such an eluent can very simply be recovered from the eluate fractions by distillation and is then directly ready for use in a subsequent elution.

When the same eluent is used during the whole elution time, an aromatic hydrocarbon or a mixture of an aliphatic or cycloaliphatic hydrocarbon with a polar organic solvent in which mixture the hydrocarbon is mainly present, is preferably used for the elution. Of the aromatic hydrocarbons are best suitable toluene and xylene, and of the cycloaliphatic hydrocarbons, cyclohexane is best suitable; of the aliphatic hydrocarbons are to be preferred branched or non-branched alkanes, separately or mixed, with boiling-points of from 60° to 160° C.

As polar solvents to be mixed with the aliphatic or cycloaliphatic hydrocarbons are preferably used: ketones, esters, nitriles, alcohols, chlorinated hydrocarbons, ethers, or mixtures of these solvents, with boiling-points of from 60° to 160° C.

Upon isolating cholesterol in commercial quantities from cholesterol-containing material according to the separation method of the invention, silica gel has proved to be best suitable as a column packing, in combination with an eluent consisting of a mixture of 80–98% by volume of an aliphatic hydrocarbon with 6–9 carbon atoms and 2–20% by volume of a lower aliphatic ketone or a lower aliphatic ester. Upon isolating cholesterol in commercial quantities from an alcohol mixture obtained by saponification of wool fat or from an ester mixture obtained by re-esterification of wool fat with a lower aliphatic alcohol, the best results were obtained when an eluent was used consisting of 19 parts by volume of heptane and 1 part by volume of acetone.

The invention will now be described in greater detail, with reference to the ensuing specific examples.

EXAMPLE I

An adsorption column having a diameter of 2.5 cm was packed with 50 g of Florisil, a magnesium silicate. As a mixture to be chromatographed was used a saponification product of wool fat, the so-called unsaponifiable part of wool fat, i.e. a mixture of wool fat alcohols, with a cholesterol content of 26.1%; 5 g of this mixture were brought on the column in a solution of 10 ml of heptane. The column was then eluted at room temperature by means of gradient elution; as eluents were successively used: heptane-toluene-acetone 70:1:9 (v:v:v); gradual increase of the toluene-acetone concentration with simultaneous decrease of the heptane concentration to heptane-toluene-acetone 70:7:63 (v:v:v); toluene-acetone 1:9 (v:v); toluene-acetone 1:10 (v:v).

The elution rate was varied slightly; the flow of liquid was 0.11–0.27 l of the eluate per hour.

The total elution time was approximately 11 hours. By means of a fraction collector, equal fractions were collected, in which the presence of cholesterol by means of thin-layer chromatography was established. The main fraction of cholesterol contained 9 g of dry substance per liter of liquid. After distilling-off the solvents, 1.35 g of crude cholesterol was obtained herefrom, which is 27% by weight calculated on the weight of the starting mixture, with a content of 68.2%. The cholesterol content of this fraction, as well as in the mixture to be isolated, was determined by means of gas chromatography. Of the overall quantity of cholesterol present in the starting mixture, 70.6% by weight were found in the resulting main fraction.

EXAMPLE II

A double-walled adsorption column having a diameter of 2.5 cm was packed with 80 g of silica gel Merck 60 having a particle size of 0.063–0.2 mm. The column was heated to a temperature of 40° C. by passing warm water through the column jacket. As a mixture to be chromatographed was used a re-esterification product of wool fat obtained by re-esterifying wool fat with methanol, with a cholesterol content of 12.7%; 32 g of this mixture were brought on the column in a solution of 64 ml of heptane-acetone 19:1 (v:v). The column was then eluted at a constant temperature of 40° C. with a mixture of heptane-acetone of 19:1 (v:v). The flow of liquid was 0.30 l of eluate per hour; the elution time was approximately 4 hours. By means of a fraction collector equal fractions were collected as described in Example I. The main fraction of cholesterol contained 1 g of dry substance per liter of liquid. After distilling off the mixture of solvents, 6.05 g of crude cholesterol were obtained herefrom, which is 18.9% by weight calculated on the weight of the starting mixture, with a content of 64.1%. Of the overall quantity of cholesterol present in the starting mixture, 95.3% by weight were found in the resulting main fraction.

EXAMPLE III

A double-walled adsorption column having a diameter of 3.4 cm was packed with 80 g of the packing material described in Example II. The column was heated at a temperature of 50° C. As a mixture to be chromatographed was used a saponification product of wool fat with a cholesterol content of 27.2%; 32 g of this mixture was brought on the column in a solution of 64 ml of heptane-acetone 19:1 (v:v).

The column was then eluted at a constant temperature of 50° C. with a heptane-acetone mixture of 19:1 (v:v). The liquid flow was 0.54 l of eluate per hour; the elution time was approximately 3.5 hours. By means of a fraction collector, equal fractions were collected as described in Example I.

The main fraction of cholesterol contained 9 g of dry material per liter of liquid. After distilling-off the solvent mixtures, 11.88 g of crude cholesterol were obtained herefrom, which is 37.1% by weight calculated on the weight of the mixture from which was started, with a content of 69.1%. Of the overall quantity of cholesterol present in the starting mixture, 94.0% by weight were found in the resulting main fraction.

EXAMPLE IV

An adsorption column as described in Example I was packed with 100 g of the packing material described in Example II. As a mixture to be chromatographed was used a saponification product of wool fat having a cholesterol content of 25.8%; 20 g of this mixture were brought on the column in a solution of 20 ml of heptane-n-butyl-acetate 4:1 (v:v).

The column was then eluted at room temperature with a mixture of heptane and n-butyl acetate 5:1 (v:v). The liquid flow was 0.23 l of eluate per hour; the elution time was approximately 7 hours. Equal fractions were collected by means of a fraction collector as described in Example I.

The main fraction of cholesterol contained 11 g of dry substance per liter of liquid. After distilling-off the solvent mixture, 5.98 g of crude cholesterol were obtained herefrom, which is 29.9% by weight calculated on the weight of the starting mixture, with a content of 79.6%. Of the overall quantity of cholesterol present in the starting mixture, 92.2% by weight were found in the resulting main fraction.

EXAMPLE V

An adsorption column as described in Example I was packed with 100 g of the packing material described in Example II in toluene. As a mixture to be chromatographed was used a saponification product of wool fat having a cholesterol content of 25.8%; 30 g of this mixture were brought on the column in a solution of 30 ml of toluene. The column was then eluted at room temperature with toluene. The liquid flow was 0.32 l of eluate per hour; the elution time was approximately 7.5 hours. Equal fractions were collected by means of a fraction collector as described in Example I.

The main fraction of cholesterol contained 6 g of dry substance per liter of liquid. After distilling-off the solvent, 7.87 g of crude cholesterol were obtained herefrom, which is 26.2% by weight calculated on the weight of the starting mixture, having a content of 81.3%.

Of the overall quantity of cholesterol present in the starting mixture, 82.7% by weight were found in the resulting main fraction.

The same adsorption column was used for a subsequent separation without a pre-treatment, in which the same quantity of the same mixture was brought on the column. The elution was carried out in the same manner as in the first experiment.

The main fraction of cholesterol now contained 9 g of dry substance per liter of liquid. After distilling-off the solvent, 7.57 g of crude cholesterol were obtained herefrom, which is 25.2% by weight calculated on the weight of the starting mixture, having a content of 82.1%.

Of the overall quantity of cholesterol present in the starting mixture, 80.3% by weight were found in the resulting main fraction.

EXAMPLE VI

An adsorption column having an inside diameter of 2.22 cm was packed with 100 g of alumina Merck Art.

1097. As a mixture to be chromatographed was used a solution of 10 g of product having a cholesterol content of 67.5% in 25 ml of toluene. The cholesterol-containing product was obtained by combining various cholesterol fractions obtained by chromatographic separation of saponified wool fat. The column was then eluted at room temperature with toluene. The liquid flow was 0.30 l of eluate per hour; the elution time was approximately 6 hours. Equal fractions were collected by means of a fraction collector as described in Example I.

The main fraction of cholesterol contained 4 g of dry substance per liter of liquid. After distilling-off the solvent, 5.93 g of crude cholesterol were obtained herefrom with a content of 78.7%. The same adsorption column was successively used without a pre-treatment for three subsequent separations, each time with the same quantity of the same starting mixture. After elution, main fractions of cholesterol were obtained of 3.79, 5.05 and 5.33 g with contents of 84.7, 84.6 and 84.1% respectively.

EXAMPLE VII

An adsorption column as described in Example II was packed with 160 g of the packing material described in Example II. As a mixture to be chromatographed was used a saponification product of wool fat with a cholesterol content of 24.9%; 64 g of this mixture were brought on the column in a solution of 128 ml of heptane-acetone 19:1 (v:v). The column was then eluted at room temperature with a heptane-acetone mixture of 19:1 (v:v). The liquid flow was 0.44 l of eluate per hour. The total experiment took 6.5 hours. The elution was followed by means of a polarimeter. The main fraction contained 11 g of dry substance per liter of liquid. After distilling-off the solvent, 22.3 g of crude cholesterol were obtained herefrom having a content of 70.0%. Of the overall quantity of cholesterol present in the starting mixture, 97.8% by weight were found in the resulting main fraction.

EXAMPLE VIII

An adsorption column as described in Example I was packed with 80 g of the packing material described in Example II. As a mixture to be chromatographed was used a saponified distillation residue of animal fatty acids, a so-called tallow residue, with a cholesterol content of 50.0%; 16 g of this mixture were brought on the column in a solution of 64 ml of heptane-acetone 19:1 (v:v).

The column was then eluted at 40° C. with a heptane-acetone mixture of 18:2 (v:v). The liquid flow was 0.26 l of eluate per hour; equal fractions were collected by means of a fraction collector as described in Example I.

The main fraction of cholesterol contained 28 g of dry substance per liter of liquid. After distilling-off the solvent, 8.13 g of crude cholesterol were obtained herefrom with a content of 83.0%. Of the overall quantity of cholesterol present in the starting mixture, 84.3% by weight were found in the resulting main fraction.

EXAMPLE IX

An adsorption column having a diameter of 30 cm was packed with 20 kg of the packing material described in Example II. As a mixture to be chromatographed was used a saponification product of wool fat with a cholesterol content of 24.5%; 8.0 kg of this mixture were brought on the column in a solution of heptane-acetone 19:1 (v:v) in 30 minutes.

The column was then eluted at room temperature with a heptane-acetone mixture of 19:1 (v:v). The liquid flow was 70 l of eluate per hour. The elution was followed by rotation measurements and refraction measurements directly in the eluate flow by means of a polarimeter and a refractometer.

The main fraction of cholesterol contained approximately 15 g of dry substance per liter of liquid. After distilling-off the solvent, 2.53 kg of crude cholesterol were obtained herefrom with a content of 73.7%. Of the overall quantity of cholesterol present in the starting mixture, 93.9% by weight were found in the resulting main fraction.

The same adsorption column was used successively without a pre-treatment for two subsequent separations, each time with the same quantity of the same starting material. After elution, main fractions of crude cholesterol were obtained of 2.37 and 2.29 kg having contents of 72.8 and 73.7%, respectively. Of the overall quantities of cholesterol present in the provided starting mixtures, 86.8 and 84.6% by weight, respectively, were found in said main fractions.

EXAMPLE X

An adsorption column as described in Example IX was packed with 32 kg of the packing material described in Example II. As a mixture to be chromatographed was used a saponification product of wool fat having a cholesterol content of 24.9%; 12.8 kg of this mixture were brought on the column in a solution of heptane-acetone 19:1 (v:v) in 30 minutes. The column was then eluted at room temperature with a heptane-acetone mixture of 19:1 (v:v). The liquid flow was 70 l of eluate per hour. The elution was followed as described in Example IX. The main fraction of cholesterol contained 17 g of dry substance per liter of liquid. After distilling-off, crude cholesterol was obtained with the weight and content as recorded in Experiment No. 1 of the table below.

The same adsorption column was used successively without a pre-treatment for another 5 subsequent separations (Experiment Nos. 2 to 6 of the table below), each time with the same quantity of the same starting material. After elution, the results recorded in the table were obtained. In experiments 5 and 6 the elution was carried out with a larger flow of liquid, namely of 210 l of eluate per hour. After experiment no. 6 the column packing was regenerated by rinsing the column with acetone. After regeneration of the column packing, the column was still used for a subsequent separation (experiment no. 7) with the results recorded in the table.

In the first column of the table below are recorded the weights of crude cholesterol from the resulting main fractions, and the contents thereof are recorded in the second column. The numbers in the third column indicate the weight percentages of cholesterol calculated on the overall quantities of cholesterol in the provided starting mixtures.

TABLE

| | Main fraction of cholesterol | | |
|---|---|---|---|
| experiment no. | weight (kg) | cholesterol content (%) | Wt. % of cholesterol calculated on starting mixture |
| 1 | 4.05 | 75 | 95 |
| 2 | 4.15 | 71 | 93 |
| 3 | 4.18 | 70 | 92 |
| 4 | 4.37 | 68 | 93 |
| 5 | 4.24 | 67 | 89 |
| 6 | 4.37 | 67 | 92 |

TABLE-continued

| | | Main fraction of cholesterol | |
|---|---|---|---|
| experiment no. | weight (kg) | cholesterol content (%) | Wt. % of cholesterol calculated on starting mixture |
| 7 | 3.86 | 75 | 91 |

EXAMPLE XI

Crystallization experiments with cholesterol obtained by chromatographic separation.

(a) 12.00 g of crude cholesterol having a content of 49.6% were dissolved, while boiling, in 30 ml of ethanol. The solution was cooled to 15° C. in 3 hours stirring. The formed crystalline precipitate was filtered off and washed with 15 ml of ethanol of approximately 15° C. 5.07 g of crystallisate having a cholesterol content of 88.3% were obtained; crystallization yield 42.3%. The cholesterol yield, i.e. the yield of pure cholesterol in the crystallisate calculated on pure cholesterol in the starting material, was 75.2%.

(b) 100.0 g of crude cholesterol having a content of 67.6% were dissolved in 300 ml of acetone while boiling. The solution was cooled to approximately 20° C. in 3 hours while stirring, was then left to stand overnight at room temperature, and was finally cooled to 15° C. in 1 hour while stirring. The formed crystalline precipitate was filtered off and washed with 100 ml of acetone. After drying in air at 80° C., 68.1 g of crystallisate were obtained having a cholesterol content of 88.8%; melting range 142.3°–145.0° C. The crystallization yield was 68.1%, the cholesterol yield was 89.5%.

(c) 200.0 g of crude cholesterol having a content of 70.5% were dissolved in 600 ml of acetic acid while heating. The solution was cooled to approximately 20° C. in 4 hours with stirring, was then left to stand overnight at room temperature, and was finally cooled to 15° C. in 1 hour while stirring. The formed crystalline precipitate was filtered off and washed successively with 200 ml of acetic acid and three times with 200 ml of water. After drying in air at 80° C., 140.2 g of crystallisate were obtained having a cholesterol content of 95.5%; melting range 147.2°–148.0° C. The crystallization yield was 70.1%; the cholesterol yield was 95.0%.

(d) 100.0 g of crude cholesterol having a content of 72.4% were dissolved, while boiling, in a mixture of 120 ml of isopropanol and 180 ml of methanol. The solution was cooled to approximately 20° C. in 3 hours while stirring, was then left to stand overnight at room temperature, and was finally cooled to 15° C. in 1 hour with stirring. The formed crystalline precipitate was filtered off and washed with a mixture of 40 ml of isopropanol and 60 ml of methanol. After drying in air at 80° C., 70.0 g of crystallisate were obtained having a cholesterol content of 93.2%; melting range 145.9°–147.0° C. The crystallization yield was 70.0%, the cholesterol yield was 90.1%.

EXAMPLE XII

A double-walled adsorption column having an internal diameter of 2.5 cm was packed with 80 g of silica gel (Merck art. 7734). The column was heated to a temperature of 25° C. by passing warm water through the column jacket. As a mixture to be chromatographed was used a saponification product from crude soya bean oil, with a content of vegetable sterols of 35.1%, viz. sito-, campe- and stigmasterol of 18.9, 8.1 and 8.1% respectively; 26.7 g of this mixture was brought on the column in a solution of 62 ml of toluene-acetone 29:1 (v:v). The column was then eluted by means of gradient elution with a mixture of toluene-acetone 29:1 (v:v), gradually changing to 2:1 (v:v). The flow of liquid was 0.5 l of eluate per hour; the total elution time was approximately 4 hours. As a main fraction 493 ml of eluate was collected, containing 11.2 g of dry substance with a sterol content of 82.3% (sito-, campe- and stigmasterol 44.6, 19.0 and 18.8% respectively). Of the overall quantity of sterols present in the starting mixture, 98.2% by weight were found in the main fraction.

EXAMPLE XIII

An adsorption column as described in Example II was packed with 80 g of the packing material described in Example II in a mixture of toluene and acetone in a ratio of 29:1 (v:v). As a mixture to be chromatographed was used a saponification product from a mixed distillation pitch of fatty acids from vegetable oils, with a content of vegetable sterols of 31.9%, viz. sito-, campe- and stigmasterol of 21.0, 7.4 and 3.5% respectively; 30.2 g of this mixture was brought on the column in a solution of 64 ml of toluene-acetone 29:1 (v:v). The column was then eluted at 25° C. by means of gradient elution with a mixture of toluene-acetone 29:1 (v:v), gradually changing to 2:1 (v:v). The flow of liquid was 0.5 l of eluate per hour; the total elution time was approximately 4 hours. As a main fraction 950 ml of eluate was collected, containing 13.6 g of dry substance with a content of vegetable sterols of 69.0% (sito-, campe- and stigmasterol 45.5, 15.7 and 7.8% respectively). Of the overall quantity of sterols present in the starting mixture, 97.5% by weight were found in the main fraction obtained.

EXAMPLE XIV

An adsorption column as described in Example II was packed with 80 g of the packing material described in Example II in a mixture of toluene and acetone in a ratio of 29:1 (v:v). As a mixture to be chromatographed was used a saponification product from a mixed distillation pitch of fatty acids from animal and vegetable oils and fats, with a cholesterol content of 20.4% and a content of vegetable sterols, viz. sito-, campe- and stigmasterol, of 12.5%; 28.6 g of this mixture was brought on the column in a solution of 64 ml of toluene-acetone 29:1 (v:v). The column was then eluted at room temperature by means of gradient elution with a mixture of toluene-acetone 29:1 (v:v), gradually changing to 2:1 (v:v). The flow of liquid was 0.5 l of eluate per hour; the total elution time was a good 4 hours. As a main fraction 636 ml of eluate was collected, containing 10.25 g of dry substance with a cholesterol content of 52.0% and a content of vegetable sterols of 30.5%. Of the overall quantity of cholesterol present in the starting mixture, 91.4% by weight were found in the main fraction obtained.

EXAMPLE XV

An adsorption column as described in Example I was packed with 165 g of silica gel in a mixture of heptane and acetone 19:1 (v:v). As a mixture to be chromatographed 40.6 g of a saponification product of wool fat with an isocholesterol content of 22.2% was brought on the column in a solution of approximately 85 ml of a mixture of heptane and acetone. The column was then eluted with a mixture of heptane-acetone 19:1 (v:v). The flow of liquid was 377 ml of eluate per hour; the total elution time was approximately 6 hours. During the elution 315 ml of eluate was collected in a fraction from which after distilling off the volatile constituents 7.48 g of dry substance with a content of isocholesterol (lanosterol and dihydrolanosterol) of 46.4% was obtained. This substance was recrystallized from a mixture of heptane and methanol 1:1 (v:v) and yielded 3.06 g of crystalline isocholesterol with a content of 95.3%.

I claim:

1. A method for the commercial scale isolation of at least one sterol in commercial scale quantities from a sterol-containing material, in which a solution of this material is subjected to a single chromatographic separation, followed by a simple recrystallization, comprising passing a commercial scale quantity of a solution of a sterol-containing material, selected from the group consisting of saponification and re-esterification products from animal and vegetable oils and fats, through a chromatographic separation column capable of separating said at least one sterol from the other components in the solution, said separation column containing packing material, selected from the group consisting of alumina, magnesium silicate, silica gel, and mixtures thereof, in a quantity of no more than ten times the weight of said sterol-containing material, recovering said at least one sterol in commercial scale quantities by eluting said column with an organic solvent or organic solvent mixture for said sterol, and isolating said at least one sterol by a simple recrystallization from an organic solvent or organic solvent mixture, thereby yielding said at least one sterol at a purity acceptable for pharmaceutical application.

2. The method of claim 1 wherein said at least one sterol is cholesterol, and the proportion of said sterol-containing material based on the amount of said packing material is approximately 40 weight percent.

3. The method of claim 2 wherein said cholesterol is recovered in a purity of at least approximately 67% before isolation thereof by recrystallization.

4. The method of claim 1 wherein said at least one sterol is cholesterol and said cholesterol is recovered in a purity of at least approximately 67% before isolation thereof by recrystallization.

5. The method of claim 1 wherein said sterol-containing material is passed through said chromatographic separation column at room temperature.

6. The method of claim 1 wherein said sterol-containing material is passed through said chromatographic separation column at a temperature slightly elevated above room temperature.

7. The method of claim 1 wherein no change in the composition of the eluent takes place during the elution step.

8. The method of claim 7 wherein said eluent is an aromatic hydrocarbon or a mixture of an aliphatic hydrocarbon or a cycloaliphatic hydrocarbon with a polar organic solvent, said mixture primarily containing said hydrocarbon.

9. The method of claim 8 wherein said at least one sterol is cholesterol, said packing material is silica gel, and said eluent is a mixture of a $C_6$–$C_9$ aliphatic hydrocarbon and a lower aliphatic ketone or a lower aliphatic ester, said hydrocarbon being present in a quantity of about 80 to about 98% by volume.

10. The method of claim 9 wherein the cholesterol-containing material is an alcohol mixture obtained by the saponification of wool fat or an ester mixture obtained by the re-esterification of wool fat with a lower aliphatic alcohol and said eluent is a mixture of about 19 parts by volume of heptane and about 1 part by volume of acetone.

* * * * *